United States Patent [19]
Wong

[11] Patent Number: 5,347,474
[45] Date of Patent: Sep. 13, 1994

[54] SELF-CALIBRATION OF AN NDIR GAS SENSOR

[75] Inventor: Jacob Y. Wong, Santa Barbara, Calif.

[73] Assignee: Gaztech Corporation, Goleta, Calif.

[21] Appl. No.: 762,396

[22] Filed: Sep. 19, 1991

[51] Int. Cl.$^5$ ............................................. G06F 15/20
[52] U.S. Cl. ............................. 364/571.02; 73/23.23; 364/550; 364/571.03
[58] Field of Search ................... 73/16, 23.23, 23.26; 364/550, 571.01, 571.02, 571.03

[56] References Cited

U.S. PATENT DOCUMENTS

| | | | |
|---|---|---|---|
| 3,329,005 | 7/1967 | Levy et al. | 73/23.23 |
| 3,681,577 | 8/1972 | Gasiunas | 364/571.02 |
| 3,797,300 | 3/1974 | Sato | 73/23.23 |
| 4,875,169 | 10/1989 | Synovec et al. | 73/23.23 X |
| 4,927,532 | 5/1990 | Pospisil et al. | 73/23.23 X |
| 4,941,101 | 7/1990 | Crilly | 73/23.23 X |
| 5,098,547 | 3/1992 | Bryan et al. | 204/401 |

*Primary Examiner*—Edward R. Cosimano
*Attorney, Agent, or Firm*—Daniel C. McKown

[57] ABSTRACT

Some cyclic variables include within each cycle a value that can be determined extrinsically. In such case, the sensed value may differ from the known value by an amount that is a combination of long-term drift of the sensor and random measuring error. The drift component can be evaluated and eliminated by the following method. Once each cycle, for a number of cycles, the sensor measures the variable at a time when its value should equal the extrinsically-known value. The differences are plotted versus time, and a best-fitting straight line is determined, which indicates the drift. Throughout the next cycle as the variable is continuously sensed, the drift determined from the best-fitting straight line is continuously applied to correct the sensed value.

5 Claims, 5 Drawing Sheets

SELF-CALIBRATION OF AN NDIR GAS SENSOR

BACKGROUND OF THE INVENTION

1. Field of the Invention

The present invention is in the field of measuring instruments, and specifically relates to a method for correcting the measurements made by a nondispersive infrared (NDIR) gas sensor for the effects of long-term drift.

2. The Prior Art

Many kinds of sensors experience long-term drift. Depending on the sensor, this drift may result from various causes, including: gradual chemical changes; a slow build-up of foreign matter, such as might result from exposure to water vapor, smoke, dust, etc.; and, variations in the electrical power supply, including battery degradation over time.

The classic approach to this problem is to provide within the sensor a reference channel that specifically measures the degradation caused by the aforementioned factors. However, provision of this reference channel increases the cost and complexity of the sensor.

The problem of uncompensated drift is especially serious in NDIR sensors in general and especially in carbon dioxide sensors that are used in fire detectors and in ventilation monitors, because these devices are expected to operate for long periods of time, perhaps even years, without attention. These uses require long-term stability to avert excessive false alarm rates and erratic ventilation.

Fortunately, under some conditions that are not uncommon, the situation is not hopeless. Using the method and apparatus described below, a sensor can be made to calibrate itself, and to compensate itself for long-term drift.

The method will be illustrated by an actual example in which a carbon dioxide sensor is used to determine the concentration of carbon dioxide gas in a building. The application of the method to the detection of other gases by the use of NDIR gas sensors is straightforward.

SUMMARY OF THE INVENTION

The lowest naturally-occurring concentration of carbon dioxide is found outdoors in rural areas; the concentration there is in the range of 300–500 parts per million.

Inside an office building or a residence, the presence of combustion and of people contribute to the amount of carbon dioxide in the air, so that indoor levels are usually higher than 500 parts per million.

The present invention grew out of prolonged observation of the carbon dioxide level in an office building. It has been discovered that the carbon dioxide level decreases when the people leave the building and exhibits a prolonged quiescent period thereafter. During this quiescent period, the carbon dioxide level approximates that found outdoors, typically 500 parts per million in a city. As the people return to work in the morning, the carbon dioxide level rises again in a predictable manner.

The self-calibration technique of the present invention is based on this daily cycle. First, the quiescent portion of the daily cycle is identified. The carbon dioxide level is measured at least once during the quiescent interval, and the measured values from successive days are stored. Each day a best-fitting straight line is determined by statistical methods. The slope of the straight line reflects the long-term drift rate.

The best fitting straight line is extrapolated forward through the next day, and is used to compensate the values measured throughout the next day. Calculation of the best-fitting straight line is repeated each day on a moving basis. Decisions involving the concentration of carbon dioxide are based on the compensated values determined by the above-described process.

A preferred example of the method will be described in detail below with the aid of the accompanying drawings which are provided for purposes of illustration and explanation, and not by way of limitation.

DETAILED DESCRIPTION OF THE PREFERRED EMBODIMENT

Figure 1:
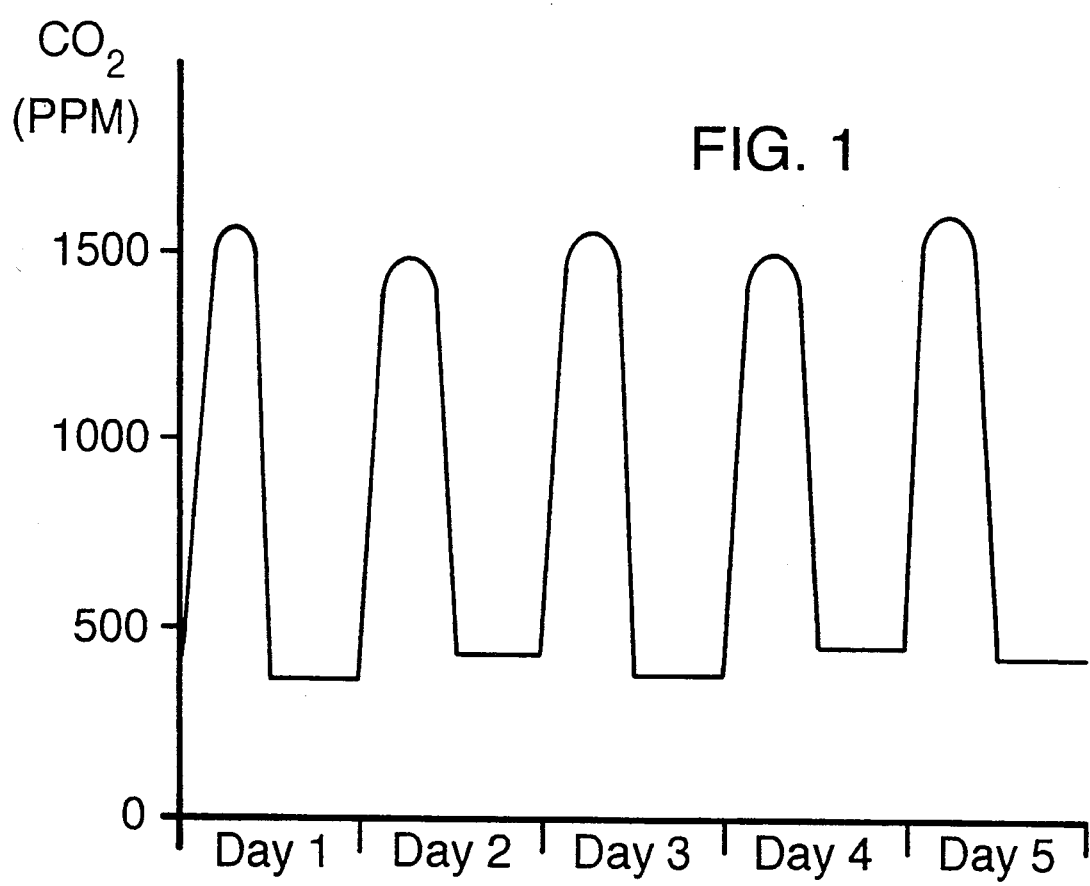
FIG. 1 is a chart illustrating typical variations in carbon dioxide concentration in a building over a period of several days.

FIG. 1 shows how the measured concentration of carbon dioxide varies during the daytime in a building, in a typical situation. Early in the morning, as the workers begin to arrive, the carbon dioxide level increases, and reaches a peak at some time during the day. Thereafter, as the workers leave the office building, the carbon dioxide level decreases, and after working hours, the carbon dioxide concentration stabilizes at a relatively low level referred to herein as a quiescent value. During the quiescent interval, the concentration of carbon dioxide is typically in the range of 300 to 500 parts per million. The effect illustrated in FIG. 1 is based on actual data observed in a number of office and business buildings.

Figure 2:
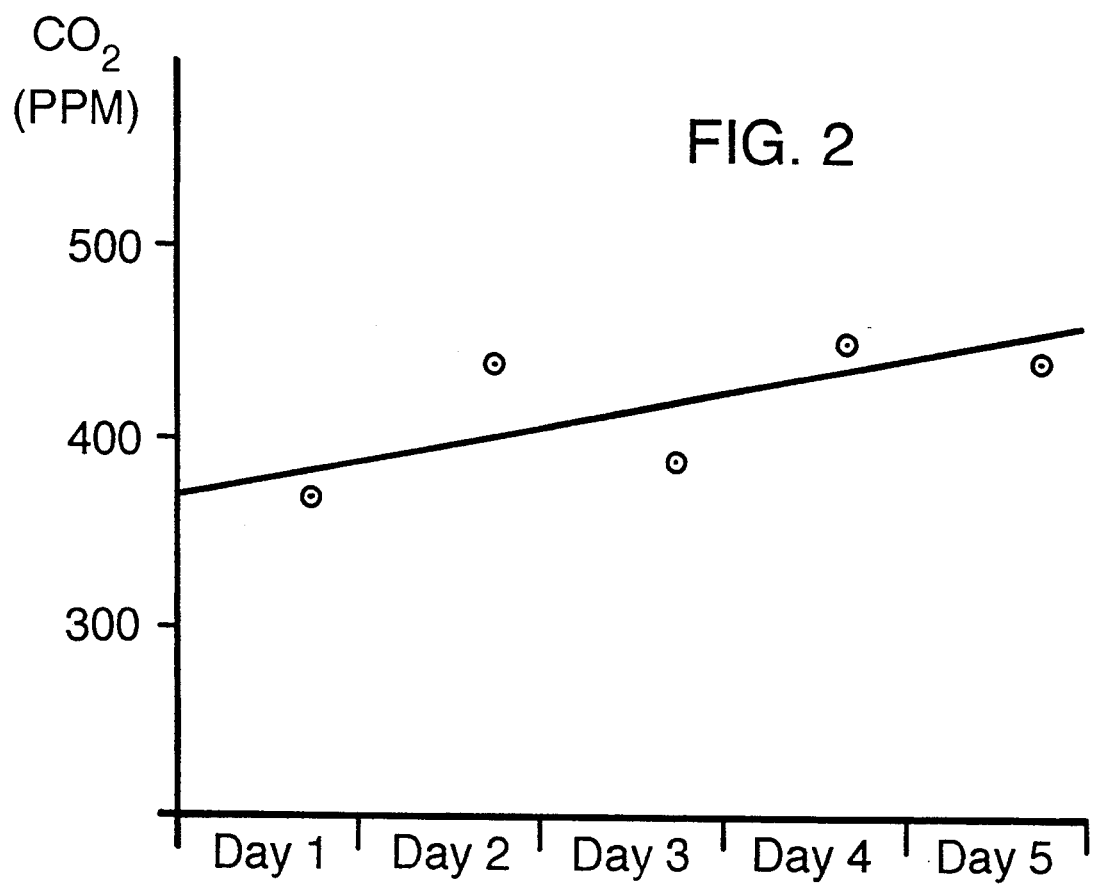
FIG. 2 is a graph showing a trend in measurements taken during the quiescent portion of successive days.

FIG. 2 shows the effect of sensor drift; the vertical scale is greatly magnified compared to FIG. 1. The data points in FIG. 2 are hypothetical readings taken by an imperfect drifting sensor during the quiescent interval on successive days. If the measuring instrument were drift-free, the data points would lie rather close to a horizontal line representing the average level of carbon dioxide during the quiescent intervals. Unfortunately, because of the drift present in a real sensor, the data points best fit a straight line having a small slope. This slope is the drift of the sensor; and in general, the drift may be upward or downward. It is the purpose of the present invention to compensate the sensor for this observed drift.

Figure 3:
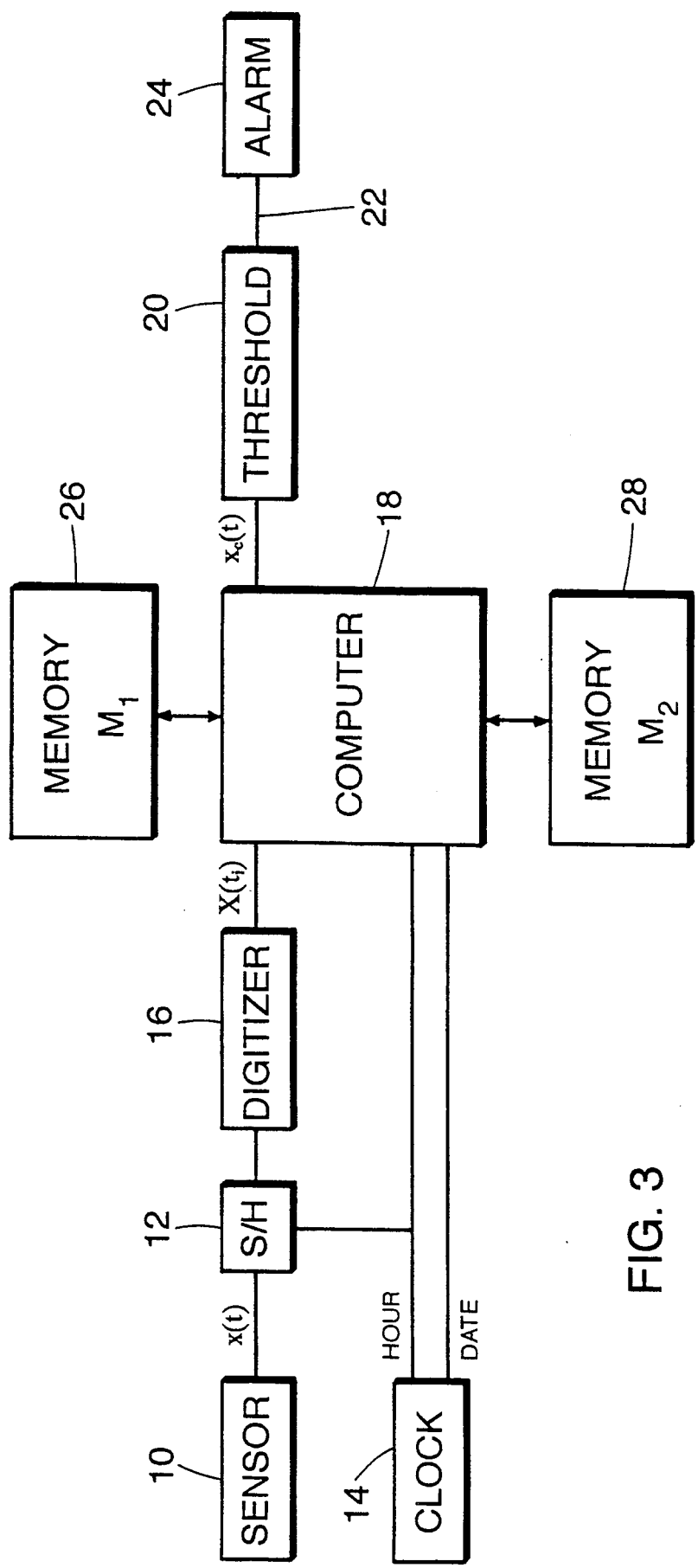
FIG. 3 is a block diagram showing a preferred embodiment of the present invention.

FIG. 3 shows the apparatus used in implementing a preferred embodiment of the present invention, and FIGS. 4 through 8 are charts a flow charts showing successive operations performed by the apparatus of FIG. 3.

A digital implementation is used in the preferred embodiment of FIG. 3 because it is believed that that approach is the simplest; however, an analog implementation is used in an alternative embodiment.

In the preferred embodiment shown in FIG. 3, the sensor 10 produces an output signal x(t) that is sampled periodically by the sample and hold circuit 12 that is enabled by the clock 14. In the preferred embodiment, the sample and hold circuit 12 captures a sample every half hour. Each captured sample, in turn, is converted to a digital form $X(t_i)$ by the digitizer 16. These successive digitized data are fed to the computer 18.

The computer 18 operates on the incoming $X(t_i)$ to compensate them for drift of the sensor 10, producing the corresponding drift-compensated $X_c(t)$. The drift-compensated variable $X_c(t)$ is then applied to a threshold circuit 20. When the threshold is exceeded, an alarm signal is produced on the line 22, and that signal is applied to operate an alarm 24 in the preferred embodiment. In an alternative embodiment, the alarm signal on the line 22 may be used to start an electric fan motor. The memories 26 and 28 are associated with the computer 18.

How the computer 18 goes about compensating for drift of the sensor is shown in the flow diagrams of FIGS. 4 through 8 in which it is assumed, for illustrative purposes, that the variable x(t) is sampled every half hour, i.e., 48 times per day.

The drift-compensating action of the present invention would normally be kept in operation at all times, and therefore the drift that accumulates in any particular day is small relative to the range of values that defines the quiescent interval. Accordingly, the measured values (including the drift component) can reasonably be expected to fall, during part of each day, within the range of values $X_L$ to $X_H$ that defines the quiescent interval.

Figure 4:
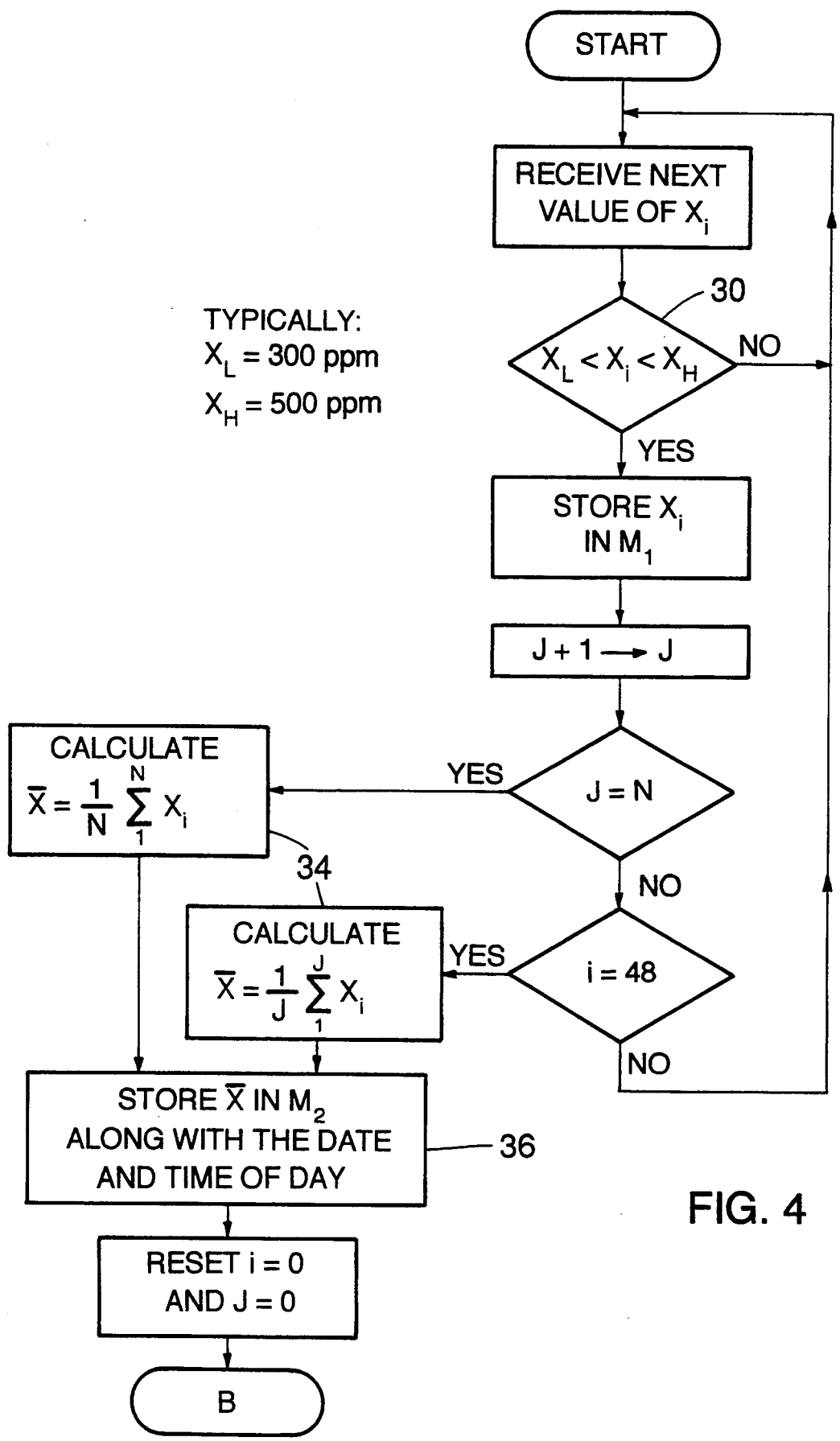
FIG. 4 is a flow chart showing a sequence of operations executed by the apparatus of FIG. 3 in a first preferred embodiment.

Thus, in the preferred embodiment, the incoming digitized samples $X(t_i)$ are first tested to determine whether they lie within the range of values that characterize the quiescent interval, as indicated at box 30 in FIG. 4.

In the preferred embodiment, a number of the samples $X(t_i)$ that have been determined to lie within the range are stored briefly in the memory M₁ 26. After a number of such samples have been stored, their average value is calculated at boxes 34 of FIG. 4, and stored in the memory M₂ 28, as the estimate, for that day, of the quiescent value (as shown in box 36 of FIG. 4). In an alternative embodiment, only one sample is taken and it is stored immediately in the memory M₂ 28 as the estimate, for that day, of the quiescent value.

The existence of a quiescent time and corresponding range of values for the carbon dioxide concentration in an office building has been verified experimentally. For variables other than carbon dioxide under a wide range of situations, a prolonged quiescent interval may not exist. Such situations are not intractable and NDIR sensors can be rendered self-calibrating in more situations than was previously thought possible.

Figure 5:
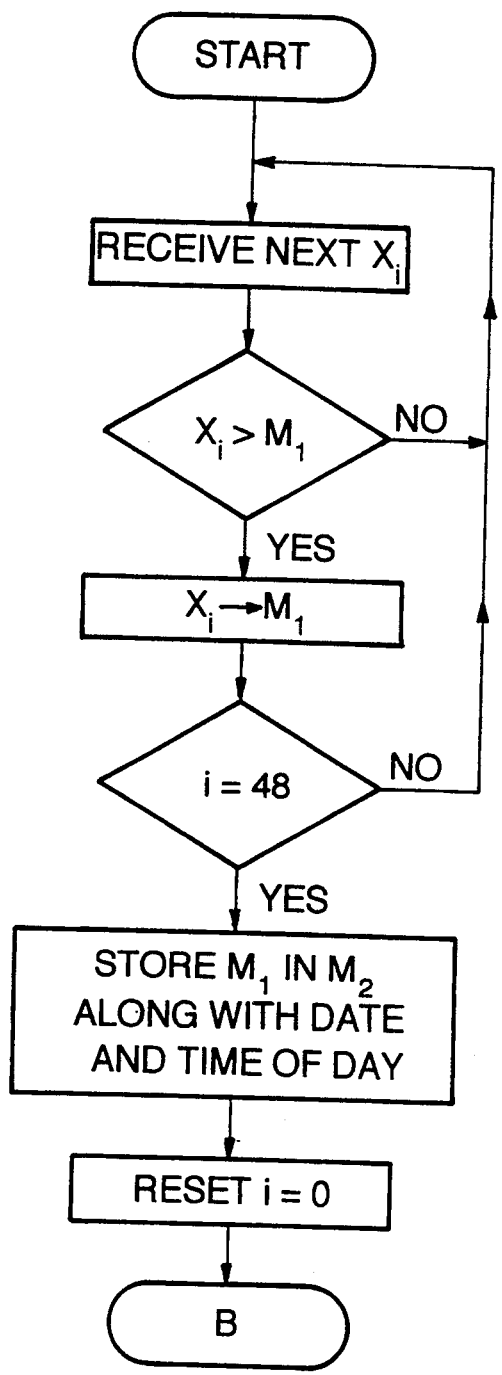
FIG. 5 is a flow chart showing a sequence of operations executed by the apparatus of FIG. 3 in a second preferred embodiment.

In some situations, it may be known in advance that the variable being measured cannot become less than or greater than some known value. For example, oxygen is not likely to exceed 21%, by weight, of the air. Likewise, water vapor is not likely to exceed a relative humidity of 100%. The flow chart of FIG. 5 is applicable to situations where a maximum or minimum is to be found each day.

Figure 6:
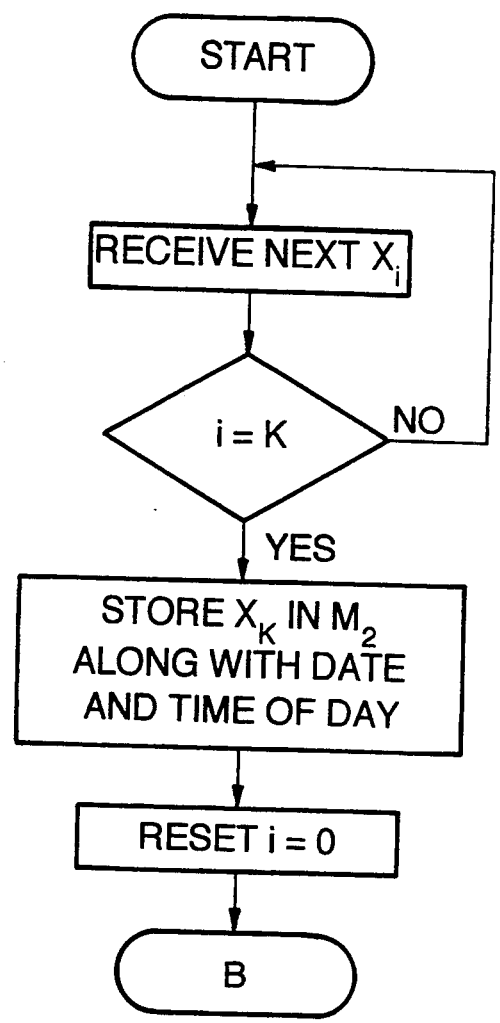
FIG. 6 is a flow chart showing a sequence of operations executed by the apparatus of FIG. 3 in a third preferred embodiment.

In still other situations, the value of a variable may be known at a particular hour of each day; for example, a starting value or an initial concentration. In this case, drift of the NDIR sensor can be determined from successive daily measurements of the variable at the particular time, in accordance with the method of the present invention, as shown in FIG. 6.

Figure 7:
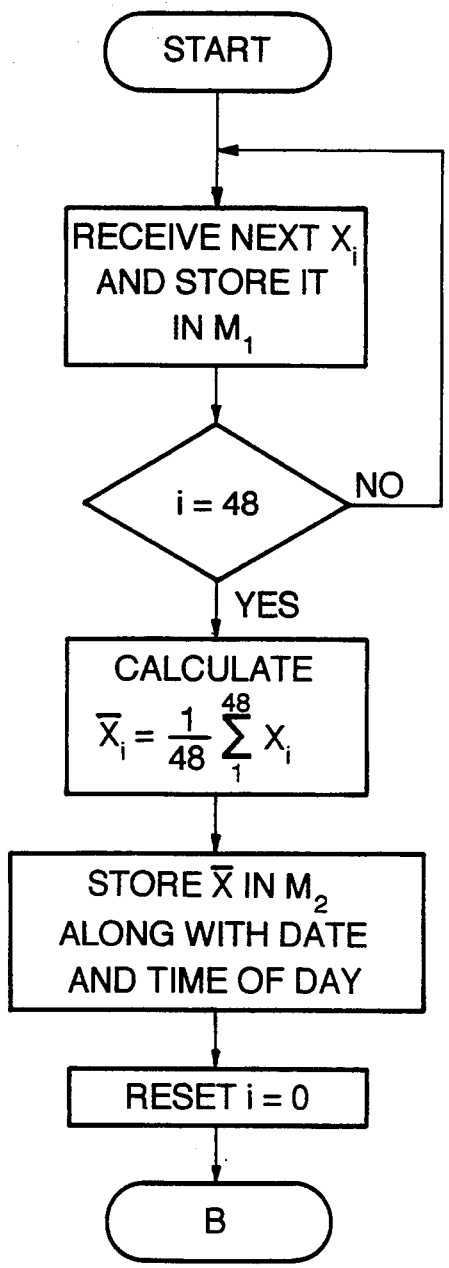
FIG. 7 is a flow chart showing a sequence of operations executed by the apparatus of FIG. 3 in a fourth preferred embodiment; and, FIG. 8 is a flow chart showing a sequence of operations executed by the apparatus of FIG. 3 in each of the preferred embodiments.

In yet other situations it may be clear from physical considerations that the total amount of gas produced each day is a constant. For example, if a known quantity of methane is burned each day in a thermostat-controlled furnace, then the total amount of water vapor produced is necessarily limited and determinable, even though the furnace is turned OFF and ON several times during the day. In this situation, the water vapor concentration measurements taken throughout the day would be totaled or averaged, as shown in FIG. 7.

The common thread that connects these examples is the idea that each day the NDIR sensor measurements are used to produce, through the computer 18, an estimate of a variable whose true value is known, at least approximately, by some other means.

The estimates found from the sensor measurements each day are stored in the memory $M_2$ 28 day by day until a selected maximum number H of the daily estimates have been stored. Thereafter, each time a new estimate is stored, the oldest one is discarded from the memory $M_2$ 28. The maximum number H is chosen, based on well-known statistical theory, to yield a desired degree of accuracy in estimating the drift.

Figure 8:
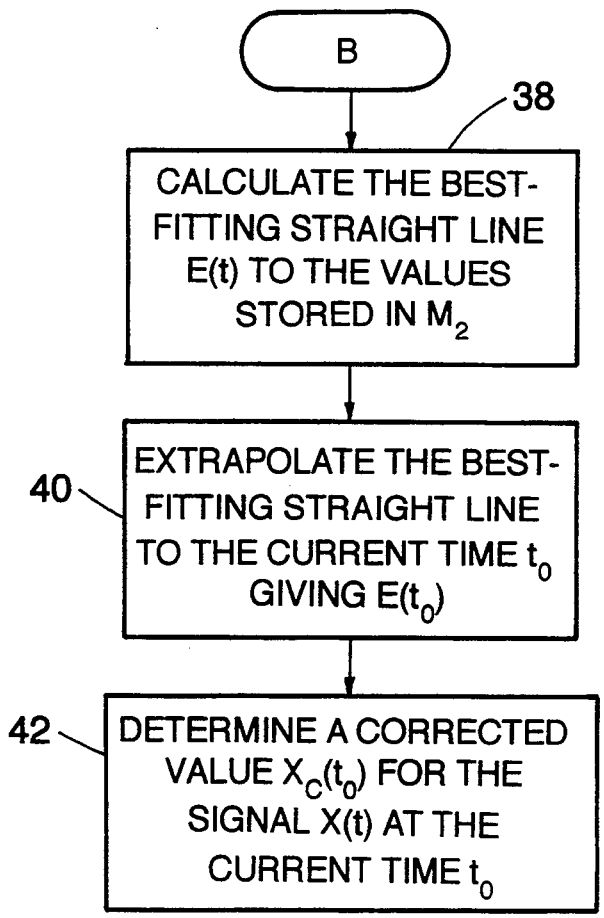

At the beginning of each day, starting with the third day, the straight line that best fits the stored estimates, is calculated and its slope is estimated, as indicated at box 38 of FIG. 8. Since the variable is presumed to have the same value each day at the time the sample is taken, the slope of the best-fitting straight line is ascribed to drift of the instrument. Using the slope thus estimated, the raw measurements taken throughout the day are corrected for the drift, as shown at boxes 40 and 42 of FIG. 8.

The drift-corrected measurements that are the output of the computer 18 are applied to the threshold circuit 20, and if the threshold is exceeded, an alarm signal is generated that is used to produce an audible or visible alarm. In another embodiment the "alarm" signal is applied to enable the operation of a fan or blower.

Thus, there has been described apparatus and a method for autonomous self-calibration of a sensor so as to increase its stability over time by correcting the raw output x(t) of the sensor to compensate for drift of the sensor. The technique is predicated on the daily or cyclical recurrence of a known value of the variable being sensed.

The foregoing detailed description is illustrative of several embodiments of the invention, and it is to be understood that additional embodiments thereof will be obvious to those skilled in the art. The embodiments described herein together with those additional embodiments are considered to be within the scope of the invention.

What is claimed is:

1. A method for drift compensation of a sensor used for measuring a cyclical variable X that is known to lie within a known range extending from a low value $x_L$ to a high value $x_H$ during a part of each cycle, said sensor producing an electrical signal x(t) representative of the instantaneous value of X at time t, said method comprising the steps of:
- a) determining when x(t) is between $x_L$ and $x_H$ where $x_L$ and $x_H$ denote the values of x(t) corresponding to $X_L$ and $X_H$ respectively;
- b) sampling x(t) during each cycle when x(t) is between $x_L$ and $x_H$ and storing a representative quiescent value of x(t) for each cycle;
- c) determining a linear function E(t) that best fits the representative quiescent values of x(t) that were stored in a number of successive cycles;
- d) extrapolating the linear function E(t) to the present time $t_0$, thereby obtaining $E(t_0)$;
- e) determining a corrected value $x_c(t_0)$ for the signal x(t) at the present time $t_0$ which is compensated for sensor drift; and,
- f) producing an enabling signal when $x_c(t_0)$ exceeds a preset threshold level.

2. A method for drift compensation of a sensor used for measuring a cyclical variable X that is known to attain a constant maximum value $X_{MAX}$ during each cycle, said sensor producing an electrical signal x(t) representative of the instantaneous value of X at time t, said method comprising the steps of:
- a) determining for each cycle the maximum value $x_{MAX}$ corresponding to $X_{MAX}$;
- b) storing the maximum values determined in successive cycles;
- c) determining a linear function E(t) that best fits the maximum values stored in a number of successive cycles;
- d) extrapolating the linear function E(t) to the present time $t_0$, thereby obtaining $E(t_0)$;
- e) determining a corrected value $x_c(t_0)$ for the signal x(t) at the present time $t_0$ which is compensated for sensor drift; and,
- f) producing an enabling signal when $x_c(t_0)$ exceeds a preset threshold level.

3. A method for drift compensation of a sensor used for measuring a cyclical variable X that is known to attain a constant minimum value $X_{MIN}$ during each cycle, said sensor producing an electrical signal x(t) representative of the instantaneous value of X at time t, said method comprising the steps of:
- a) determining for each cycle the minimum value $x_{MIN}$ corresponding to $x_{MIN}$;
- b) storing the minimum values determined in successive cycles;
- c) determining a linear function E(t) that best fits the minimum values stored in a number of successive cycles;
- d) extrapolating the linear function E(t) to the present time $t_0$, thereby obtaining $E(t_0)$;
- e) determining a corrected value $x_c(t_0)$ for the signal x(t) at the present time $t_0$ which is compensated for sensor drift; and,
- f) producing an enabling signal when $x_c(t_0)$ exceeds a preset threshold level.

4. A method for drift compensation of a sensor used for measuring a cyclical variable X that is known to attain a known particular value $X_K$ at some known phase of each cycle, said sensor producing an electrical signal x(t) representative of the instantaneous value of X at time t, said method comprising the steps of:
- a) sampling the value of x(t) once in each cycle at said known phase of each cycle;
- b) storing the values sampled in successive cycles;
- c) determining a linear function E(t) that best fits the values stored in a number of successive cycles;
- d) extrapolating the linear function E(t) to the present time $t_0$, thereby obtaining $E(t_0)$;
- e) determining a corrected value $x_c(t_0)$ for the signal x(t) at the present time $t_0$ which is compensated for sensor drift; and
- f) producing an enabling signal when $x_c(t_0)$ exceeds a preset threshold level.

5. A method for drift compensation of a sensor used for measuring a cyclical variable X that is known to have the same average value X for each cycle, said sensor producing an electrical signal x(t) representative of the instantaneous value of X at time t, said method comprising the steps of:
- a) determining the average value x of x for each cycle;
- b) storing the average values determined in step a) for each cycle;
- c) determining a linear function E(t) that best fits the average values stored in a number of successive cycles;
- d) extrapolating the linear function E(t) to the present time $t_0$, thereby obtaining $E(t_0)$;
- e) determining a corrected value $x_c(t_0)$ for the signal x(t) at the present time $t_0$ which is compensated for sensor drift; and,
- f) producing an enabling signal when $x_c(t_0)$ exceeds a preset threshold level.

* * * * *